United States Patent
Miyamoto et al.

(10) Patent No.: US 11,833,146 B2
(45) Date of Patent: Dec. 5, 2023

(54) DEMENTIA THERAPEUTIC AGENT COMBINING PYRAZOLOQUINOLINE DERIVATIVE AND DONEPEZIL

(71) Applicant: Eisai R&D Management Co., Ltd., Tokyo (JP)

(72) Inventors: Mai Miyamoto, Tsukuba (JP); Sadaharu Kotani, Tokyo (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 16/607,402

(22) PCT Filed: May 30, 2018

(86) PCT No.: PCT/JP2018/020638
§ 371 (c)(1),
(2) Date: Oct. 23, 2019

(87) PCT Pub. No.: WO2018/221545
PCT Pub. Date: Dec. 6, 2018

(65) Prior Publication Data
US 2020/0129501 A1 Apr. 30, 2020

Related U.S. Application Data

(60) Provisional application No. 62/513,692, filed on Jun. 1, 2017.

(51) Int. Cl.
*A61K 31/4745* (2006.01)
*A61P 25/28* (2006.01)
*A61K 31/445* (2006.01)

(52) U.S. Cl.
CPC ........ *A61K 31/4745* (2013.01); *A61K 31/445* (2013.01); *A61P 25/28* (2018.01)

(58) Field of Classification Search
CPC .... A61K 31/4745; A61K 31/445; A61P 25/28
USPC ................................................ 514/293, 319
See application file for complete search history.

(56) References Cited

U.S. PATENT DOCUMENTS

| | | | | |
|---|---|---|---|---|
| 5,837,724 A | * | 11/1998 | Allen ................ | A61K 31/4025 514/422 |
| 5,962,535 A | * | 10/1999 | Miyamoto ........... | A61K 31/445 514/724 |
| 8,563,565 B2 | | 10/2013 | Norimine et al. | |
| 2006/0035920 A1 | | 2/2006 | Boyle et al. | |
| 2009/0131467 A1 | | 5/2009 | Kanazawa et al. | |
| 2010/0048556 A1 | | 2/2010 | Okada et al. | |
| 2010/0210839 A1 | | 8/2010 | Boss et al. | |
| 2011/0082137 A1 | | 4/2011 | Giovannini et al. | |
| 2011/0131467 A1 | | 6/2011 | Weathers | |
| 2011/0184000 A1 | | 7/2011 | Giovannini et al. | |
| 2011/0319385 A1 | | 12/2011 | Kaizawa et al. | |
| 2013/0085134 A1 | | 4/2013 | Kaizawa et al. | |
| 2013/0143907 A1 | | 6/2013 | Norimine et al. | |
| 2013/0225553 A1 | | 8/2013 | Kaizawa et al. | |
| 2013/0225572 A1 | | 8/2013 | Okada et al. | |

(Continued)

FOREIGN PATENT DOCUMENTS

| | | |
|---|---|---|
| CA | 2754457 | 9/2010 |
| CN | 101553491 | 10/2009 |

(Continued)

OTHER PUBLICATIONS

Bourke et al., "Possible association between donepezil and worsening Parkinson's disease," The Annals of Pharmacotherapy, 1998, 32:610-611.

(Continued)

*Primary Examiner* — Charanjit Aulakh
(74) *Attorney, Agent, or Firm* — Fish & Richardson P.C.

(57) ABSTRACT

There is provided a therapeutic agent for Alzheimer's disease and Lewy body dementia for combined use of (S)-7-(2-methoxy-3,5-dimethylpyridin-4-yl)-1-(tetrahydrofuran-3-yl)-1H-pyrazolo[4,3-c]quinoline-4(5H)-one represented by formula (1):

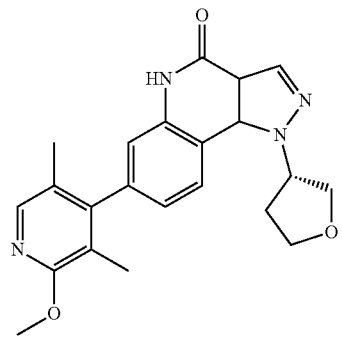

(I)

or a pharmaceutically acceptable salt thereof, and donepezil represented by formula (II):

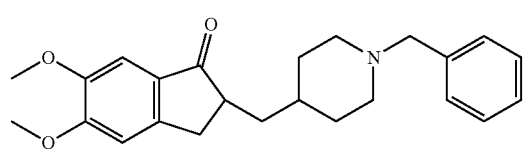

(II)

or a pharmaceutically acceptable salt thereof.

9 Claims, No Drawings

(56) References Cited

U.S. PATENT DOCUMENTS

| | | |
|---|---|---|
| 2013/0296352 A1 | 11/2013 | Norimine et al. |
| 2016/0046623 A1 | 2/2016 | Ozaki |
| 2020/0078306 A1 | 3/2020 | Schuck et al. |
| 2020/0129488 A1 | 4/2020 | Miyamoto et al. |
| 2020/0155541 A1 | 5/2020 | Miyamoto et al. |

FOREIGN PATENT DOCUMENTS

| | | | |
|---|---|---|---|
| CN | 101983199 | 3/2011 | |
| EA | 200500322 | 8/2005 | |
| EP | 1925617 | 5/2008 | |
| EP | 2103613 | 9/2009 | |
| EP | 2769980 | 8/2014 | |
| EP | 2982675 | 2/2016 | |
| JP | H5-132484 | 5/1993 | |
| JP | H9-506634 | 6/1997 | |
| JP | 2006-045118 | 2/2006 | |
| JP | 2011-516454 | 5/2011 | |
| JP | 2012-515761 | 7/2012 | |
| JP | 2013-051639 | 4/2013 | |
| JP | 2013-067595 | 4/2013 | |
| JP | 5546693 | 5/2014 | |
| MX | 2014/003800 | 7/2014 | |
| RU | 2383546 | 8/2006 | |
| RU | 2426734 | 8/2011 | |
| WO | WO 95/32205 | 11/1995 | |
| WO | WO 98/30243 A1 * | 7/1998 | ............. A61K 31/44 |
| WO | WO 2003/037899 | 5/2003 | |
| WO | WO 2007/032466 | 3/2007 | |
| WO | WO 2008/072778 | 6/2008 | |
| WO | WO 2008/072779 | 6/2008 | |
| WO | WO 2008/139293 | 11/2008 | |
| WO | WO 2009/121919 | 10/2009 | |
| WO | WO 2010/026214 | 3/2010 | |
| WO | WO 2010/084438 | 7/2010 | |
| WO | WO 2010/101230 | 9/2010 | |
| WO | WO 2012/020022 | 2/2012 | |
| WO | WO 2012/033144 | 3/2012 | |
| WO | WO 2012/110440 | 8/2012 | |
| WO | WO 2013/045400 | 4/2013 | |
| WO | WO 2013/051639 | 4/2013 | |
| WO | WO 2014/163147 | 10/2014 | |

OTHER PUBLICATIONS

Eisai Co. Ltd. [Online], "Press Conference; Materials in reporter meeting," Mar. 2017, [Retrieved on Jul. 3, 2018], Retrieved from: URL<https://www.eisai.co.jp/ir/library/presentations/pdf/4523_170309>, 96 pages (with English Translation).
Gauthier et al., "Efficacy of Donepezil on Behavioral Symptoms in Patients With Moderate to Severe Alzheimer's Disease," International Psychogeriatrics, 2002, 14(4):389-404.
Grossberg et al., "Memantine Therapy of Behavioral Symptoms in Community-Dwelling Patients with Moderate to Severe Alzheimer's Disease," Dementia and Geriatric Cognitive Disorders, 2009, 27:164-172.
Holmes et al., "The efficacy of donepezil in the treatment of neuropsychiatric symptoms in Alzheimer disease," Neurology, 2004, 63:214-219.
Homma et al., "Clinical Efficacy and Safety of Donepezil on Cognitive and Global Function in Patients with Alzheimer's Disease," Dementia and Geriatric Cognitive Disorders, 2000, 11:299-313.
Homma et al., "Donepezil Treatment of Patients with Severe Alzheimer's Disease in a Japanese Population: Results from a 42-Week, Double-Blind, Placebo-Controlled, Randomized Trial," Dementia and Geriatric Cognitive Disorders, 2007, 25:399-407.
Howard et al., "Donepezil and Memantine for Moderate-to-Severe Alzheimer's Disease," The New England Journal of Medicine, 2012, 366:893-903.
International Search Report in International Application No. PCT/JP2018/020638, dated Aug. 21, 2018, 4 pages (with English Translation).

Japanese Society of Neurology [Online], "Dementia with Lewy bodies (included Parkinson's disease)," Chapter 7, Online Dementia disease treatment guidelines, 2010, [Retrieved on Jul. 3, 2018], Retrieved from: URL<http://www.neurology-jp.org.guidelinem/deg1/sinkei_deg1_2010_08.pdf>, pp. 300-302 (with Partial Translation).
Lopez et al., "Long-term effects of the concomitant use of memantine with cholinesterase inhibition in Alzheimer disease," J Neurol Neurosurg Psychiatry, 2009, 80(6):600-607.
Mecocci et al., "Effects of memantine on cognition in patients with moderate to severe Alzheimer's disease: post-hoc analyses of ADAS-cog and SIB total and single-item scores from six randomized, double-blind, placebo-controlled studies," International Journal of Geriatric Psychiatry, 2009, 24:532-538.
Mori et al., "Donepezil for Dementia with Lewy Bodies: A Randomized, Placebo-Controlled Trial," Annals of Neurology, 2012, 72:41-52.
Raskind et al., "Galantamine in AD: A 6-month randomized, placebo-controlled trial with a 6-month extension," Neurology, 2000, 54:2261-2268.
Winblad et al., "Ideal: A 6-month, double-blind, placebo-controlled study of the first skin patch for Alzheimer disease," Neurology, 2007, 69(Suppl. 1):69:S14-S22.
Office Action in Israeli Patent Application No. 270318, dated Aug. 23, 2020, 5 pages (with English Translation).
Office Action in Israeli Patent Application No. 270357, dated Aug. 23, 2020, 5 pages (with English Translation).
Office Action in Israeli Patent Application No. 270394, dated Aug. 23, 2020, 5 ages (with English Translation).
Office Action in Israeli Patent Application No. 270395, dated Aug. 23, 2020, 5 pages (with English Translation).
Homma et al., "Donepezil Treatment of Patients with Severe Alzheimer's Disease in a Japanese Population: Results from a 42-Week, Double-Blind, Placebo-Controlled, Randomized Trial," Dementia and Geriatric Cognitive Disorders, Apr. 2008, 25:399-407.
International Preliminary Report on Patentability in International Application No. PCT/JP2018/020638, dated Dec. 12, 2019, 7 pages.
International Preliminary Report on Patentability in International Application No. PCT/JP2018/020649, dated Dec. 12, 2019, 6 pages.
International Preliminary Report on Patentability in International Application No. PCT/JP2018/020650, dated Dec. 12, 2019, 8 pages.
Office Action in U.S. Appl. No. 16/609,514, dated Oct. 2, 2020, 9 pages.
Bergman et al., "Successful Use of Donepezil for the Treatment of Psychotic Symptoms in Patients With Parkinson's Disease," Clinical Neuropharmacology, Mar.-Apr. 2002, 25(2):107-110.
Bonkale et al., "Reduced nitric oxide responsive soluble guanylyl cyclase activity in the superior temporal cortex of patients with Alzheimer's disease," Neuroscience Letters, 1995, 187:5-8.
Brandon and Rotella, "Potential CNS—14 Applications for Phosphodiesterase Enzyme Inhibitors," Annual Reports in Medicinal Chemistry, 2007, 42:3-12.
Chinese Observations in Application No. 201480016592.4, dated Nov. 4, 2015, 2 pages, (with English Translation).
Cummings et al., "Pimavanserin for patients with Parkinson's disease psychosis: a randomised, placebo-controlled phase 3 trial," The Lancet, Feb. 2014, 383(9916):533-540.
Domek-Łopacińska et al., "Cyclic GMP Metabolism and its role in brain physiology," Journal of Physiology and Pharmacology, 2005, 56:15-34.
Dubois et al., "Donepezil in Parkinson's Disease Dementia: A Randomized Double-Blind Efficacy and Safety Study," Movement Disorders, Sep. 2012, 27(10):1230-1238.
European Response to Office Action in Application No. 14780073.4, dated May 11, 2016, 5 pages.
European Response to Office Action in Application No. 14780139.3, dated May 10, 2016, 4 pages.
European Search Report in Application No. 14780073.4, dated Jul. 28, 2016, 4 pages.
European Search Report in Application No. 14780139.3, dated Jul. 13, 2016, 5 pages.
Extended European Search Report in European Application No. 12837953.4, dated Jan. 27, 2015, 10 pages.

(56) References Cited

OTHER PUBLICATIONS

Fisher et al., "Isolation and Characterization of PDE9A, a Novel Human cGMP-specific Phosphodiesterase," The Journal of Biological Chemistry, 1998, 273(25):15559-15564.
Horita et al., "Effects of the adenosine A2A antagonist istradefylline on cognitive performance in rats with a 6-OHDA lesion in prefrontal cortex," Psychopharmacology, Dec. 2013, 230(3):345-352.
Hutson et al., "The selective phosphodiesterase 9 (PDE9) inhibitor PF-04447943 (6-[(3S,4S)-4-methyl-1-(pyrimidin-2-ylmethyl)pyrrolidin-3-yl]-1-(tetrahydro-2H-pyran-4-yl)-1,5-dihydro-4H-pyrazolo[3,4-d]pyrimidin-4-one) enhances synaptic plasticity and cognitive function in rodents," Neuropharmacology, Sep. 2011, 61(4):665-676.
International Preliminary Report on Patentability in International Application No. PCT/JP2012/075748, dated Apr. 17, 2014, 10 pages.
International Preliminary Report on Patentability in International Application No. PCT/JP2014/059852, dated Oct. 15, 2015, 8 pages.
International Preliminary Report on Patentability in International Application No. PCT/JP2014/059853, dated Oct. 15, 2015, 7 pages.
International Search Report and Written Opinion in International Application No. PCT/JP2018/020643, dated Aug. 21, 2018, 4 pages.
International Search Report in International Application No. PCT/JP2012/075748, dated Nov. 20, 2012, 8 pages (with English Translation).
International Search Report in International Application No. PCT/JP2018/020649, dated Aug. 21, 2018, 3 pages (with English Translation).
International Search Report in International Application No. PCT/JP2018/020650, dated Aug. 21, 2018, 4 pages (with English Translation).
Kleiman et al., "Phosphodiesterase 9A Regulates Central cGMP and Modulates Responses to Cholinergic and Monoaminergic Perturbation in Vivo," J Pharmacol. Exp. Thera., Feb. 9, 2012, 341(2):396-409.
McKeith et al., "Diagnosis and management of dementia with Lewy bodies: third report of the DLB Consortium," Neurology, Dec. 2005, 65(12):1863-1872.
McKeith et al., "Efficacy of rivastigmine in dementia with Lewy bodies: a randomised, double-blind, placebo-controlled international study," The Lancet, Dec. 2000, 356(9247):2031-2036.
Neurology-jp.org [online], "Dementia with Lewy bodies included Parkinson's disease," 2010, [Retrieved on Jan. 16, 2020], retrieved from: URL<http://www.neurology-jp.org/guidelinem/degl/sinkei_degl_2010_08.pdf>, pp. 300-302 (with English Translation).
Notice of Allowance in Australian Patent Application No. 2012319549, dated Jul. 19, 2016, 3 pages.
Notice of Allowance in Israeli Patent Application No. 231650, dated Feb. 10, 2016, 5 pages, (with English Translation).
Notice of Allowance in Japanese Patent Application No. P2013-537544, dated Apr. 30, 2014, 6 pages, (with English Translation).
Notice of Allowance in Russian Patent Application No. 2014112931, dated Aug. 22, 2016, 19 pages, (with English translation).
Notice of Allowance in Singaporean Patent Application No. 11201400717Q, dated May 26, 2016, 4 pages.
Notice of Allowance in South African Patent Application No. 2014/02439, dated Jan. 21, 2015, 3 pages.
Notice of Allowance in Taiwanese Patent Application No. 101136747, dated Aug. 17, 2016, 5 pages, (with English Translation).
Notice of Allowance in U.S. Appl. No. 13/644,745, dated Jun. 10, 2013, 13 pages.
Office Action in Australian Patent Application No. 2012319549, dated Jun. 1, 2016, 7 pages.
Office Action in Chilean Patent Application No. 2014-00821, dated Oct. 29, 2015, 11 pages, (with English Translation).
Office Action in Chinese Patent Application No. 201280046653.2, dated Feb. 28, 2015, 10 pages, (with English Translation).
Office Action in Chinese Patent Application No. 201480016592.4, dated May 12, 2016, 12 pages, (with English Translation).
Office Action in Chinese Patent Application No. 201480016592.4, dated Oct. 16, 2015, 2 pages, (with English Translation).
Office Action in Chinese Patent Application No. 201480017423.2, dated Mar. 1, 2016, 10 pages, (with English Translation).
Office Action in Colombian Patent Application No. 14-059034, dated Mar. 10, 2015, 13 pages, (with English translation).
Office Action in Filipino Patent Application No. 1-2014-500580, dated Jun. 17, 2016, 3 pages.
Office Action in Golf Cooperation Council Patent Application No. GC2012-22447, dated Apr. 21, 2016, 4 pages.
Office Action in Israeli Patent Application No. 231650, dated Jul. 16, 2014, 4 pages, (with English Translation).
Office Action in Israeli Patent Application No. 241695, dated Jan. 24, 2016, 5 pages, (with English Translation).
Office Action in Israeli Patent Application No. 241796, dated Jan. 24, 2016, 5 pages, (with English Translation).
Office Action in Japanese Patent Application No. P2014-538559, dated Sep. 30, 2014, 4 pages, (with English Translation).
Office Action in New Zealand Patent Application No. 622594, dated Feb. 4, 2015, 2 pages.
Office Action in Pakistani Patent Application No. 672/2012, dated Feb. 14, 2013, 8 pages.
Office Action in Taiwanese Patent Application No. 101136747, dated Apr. 22, 2016, 5 pages, (with English Translation).
Office Action in U.S. Appl. No. 13/644,745, dated Mar. 26, 2013, 8 pages.
Office Action in Vietnamese Patent Application No. 1-2015-03459, dated Nov. 25, 2015, 2 pages, (with English Translation).
"PF-04447943: A Phase 2 Controlled Clinical Trial of a Selective PDE9A Inhibitor in Alzheimer's Disease, Apr. 6, 2005," Abstract of Alzheimer's Association International Conference (AAIC) 2011, Jul. 16-21, 2011; Pair, France, 1 page.
Perry et al., "Neocortical cholinergic activities differentiate Lewy body dementia from classical Alzheimer's disease," Neuroreport, Mar. 1994, 5(7):747-749.
Response filed in Chilean Office Action in Application No. 2014-00821, dated Aug. 19, 2015, 26 pages, (with English Translation).
Response filed in Chilean Office Action in Application No. 2014-00821, dated Dec. 16, 2015, 6 pages, (with English Translation).
Response to Examination Report in Australian Patent Application No. 2012319549, dated Jul. 8, 2016, 6 pages.
Response to Extended European Search Report in European Patent Application No. 12837953.4, dated May 15, 2015, 22 pages.
Response to Office Action filed in Chinese Patent Application No. 201280046653.2, dated Apr. 28, 2015, 16 pages, (with English Translation).
Response to Office Action filed in Colombian Patent Application No. 14-059034, dated Jul. 16, 2015, 23 pages, (with English translation).
Response to Office Action in Israeli Patent Application No. 231650, dated Nov. 6, 2014, 8 pages, (with English Translation).
Response to Office Action in Israeli Patent Application No. 241695, dated May 23, 2016, 4 pages (with English Translation).
Response to Office Action in Israeli Patent Application No. 241796, dated May 23, 2016, 4 pages (with English Translation).
Response to Office Action in New Zealand Patent Application No. 622594, dated May 22, 2015, 16 pages.
Response to Office Action in Russian Patent Application No. 2014112931, dated Jul. 26, 2016, 23 pages, (with English Translation).
Response to Office Action in Vietnamese Patent Application No. 1-2015-03459, dated Dec. 17, 2015, 21 pages, (with English translation).
Sambeth et al., "Cholinergic drugs affect novel object recognition in rats: Relation with hippocampal EEG?," European Journal of Pharmacology, Oct. 2007, 572(2-3):151-159.
Shimada et al., "Mapping of brain acetylcholinesterase alterations in Lewy body disease by PET," Neurology, Jul. 2009, 73(4):273-278.
Singapore Request to Amend Application Before Grant in Application No. 11201400717Q, dated Feb. 12, 2016, 9 pages.
Snyder et al., "Reversal of scopolamine-induced deficits with a single dose of donepezil, an acetylcholinesterase inhibitor," Alzheimer's & Dementia, Oct. 2005, 1(2):126-135.
Submission Document in Filipino Patent Application No. 1-2014-500580, dated Aug. 30, 2016, 3 pages.

(56) References Cited

OTHER PUBLICATIONS

Submission Document in Filipino Patent Application No. 1-2014-500580, dated Jul. 21, 2016, 5 pages.
Submission Document in Gulf Cooperation Council Patent Application No. GC2012-22447, dated Jul. 18, 2016, 4 pages, (with English Translation).
Submission Document in Malaysian Patent Application No. PI2014700702, dated Sep. 28, 2016, 12 pages, (with English Translation).
Submission Document in Pakistani Patent Application No. 672/2012, dated Jul. 28, 2016, 17 pages, (with English Translation).
Submission Document in Taiwanese Patent Application No. 101136747, dated Jul. 21, 2016, 15 pages, (with English Translation).
Submission Document in Thai Patent Application No. 1401001864, dated Feb. 15, 2016, 352 pages, (with English Translation).
Submission Documents in Chinese Patent Application No. 2014/80017423.2, dated Jul. 4, 2016, 6 pages, (with English Translation).
Takano et al., "Oral Absorption of Poorly Water-Soluble Drugs: Computer Simulation of Fraction Absorbed in Humans From a Miniscale Dissolution Test," Pharm Res, Jun. 2006, 23(6):1144-1156.
Tiraboschi et al., "Cholinergic dysfunction in diseases with Lewy bodies," Neurology, Jan. 2000, 54(2):407-411.
Van der Staay et al., "The novel selective PDE9 inhibitor BAY 73/6691 improves learning and memory in rodents," Neuropharmacology, 2008, 55:908-918.
Wang et al., "Cyclic GMP-Dependent Protein Kinase and Cellular Signaling in the Nervous System," Journal of Neurochemistry, 1997, 68:443-456.
Ando et al., "Preclinical Characterization of E2027, a Novel Phosphodiesterase 9 Inhibitor," Alzheimer's & Dementia: the Journal of the Alzheimer's Association, Jul. 2017, 13(7):XP085217616, 1 page.
Office Action in Mexican Patent Application No. MX/a/2019/013198, dated Oct. 5, 2020, 7 pages (with English Translation).
Search Report in European Patent Application No. 18810202.4, dated Nov. 23, 2020, 9 pages.
Submission Document in Israeli Patent Application No. 270318, dated Nov. 16, 2020, 55 pages (with English Translation).
Submission Document in Israeli Patent Application No. 270357, dated Dec. 7, 2020, 5 pages (with English Translation).
Submission Document in Israeli Patent Application No. 270394, dated Nov. 15, 2020, 40 pages (with English Translation).
Submission Document in Israeli Patent Application No. 270395, dated Nov. 17, 2020, 35 pages (with English Translation).
Submission Document in Mexican Patent Application No. MX/a/2019/013198, dated Dec. 2, 2020, 12 pages (with English Translation).
Submission Document in U.S. Appl. No. 16/609,514, dated Nov. 25, 2020, 11 pages.
[No Author Listed], "Eisai Scientific Meeting 2019," Presentation, Eisai Co., Ltd., Apr. 23, 2019, 137 pages.
Ando et al., "Effects of repeated administration of E2027, a novel phosphodiesterase-9 inhibitor, on cyclic GMP levels in rat cerebrospinal fluid," Poster presented at Alzheimer's Association International Conference (AAIC), Chicago, IL, Jul. 22-26, 2018, P3-062, 1 page.
Ando et al., "Preclinical characterization of E2027, a novel phosphodiesterase (PDE) 9 inhibitor," Poster presented at Alzheimer's Association International Conference (AAIC), Jul. 16-20, 2017, P3-043, 1 page.
Chiu et al., "Donepezil in the one-year treatment of dementia with Lewy bodies and Alzheimer's disease," Journal of Neurological Sciences, 2017, 381:p322, XP085294732, 1 page.
Goto et al., "Effect of E2027, a Novel Phosphodiesterase-9 Inhibitor, on Cognitive Function and Hippocampal Cyclic GMP in Tg2576 Mouse Model of Alzheimer's Disease," Poster presented at 15th International Conference on Alzheimer's & Parkinson Disease (AD/PD), Virtual Conference, Mar. 9-14, 2021, P153, 1 page.
Lai et al., "Phase 1 Investigation into the Safety, Tolerability, Pharmacokinetics (PK) and Pharmacodynamics (PD) of E2027, a Selective Phosphodiesterase-9 (PDE9) Inhibitor," Presentation slides presented at Alzheimer's Association International Conference (AAIC), Jul. 16-20, 2017, pp. 1-10.
Landry et al., "Concentration Response Modeling of Ecg Data for E2027 To Inform Dose Sft Ection for Phase 2 Dementia in Lewy Body Study," Poster presented at 14th International Conference on Alzheimer's & Parkinson's Diseases, (AD/PD 2019), Lisbon, Portugal, Mar. 26-31, 2019, 1 page.
Landry et al., "E2027, a novel phosphodiesterase-9 (PDE9) inhibitor in development for treatment of dementia with Lewy bodies (DLB), showed No. clinically significant drug interaction with diltiazem," Poster presented at Alzheimer's Association International Conference (AAIC), Chicago, IL, Jul. 22-26, 2018, Pl-055, 1 page.
Landry et al., "Phase 1 Multiple Ascending Dose (MAD) Study of Phosphodiesterase-9 Inhibitor E2027: Confirmation of Target Engagement and Selection of Phase 2 Dose in Dementia with Lewy Bodies," Presentation slides presented at Alzheimer's Association International Conference (AAIC), Jul. 22-26, 2018, pp. 1-10.
Magierskr et al., "1.206—Donepezil versus rivastigmrne tolerability study in dementia with Lewy bodies and Alzheimer's disease," Parkinsonism and Related Disorders, Elsevier Science, Oxford, GB, 2007, 13:S62, XP022635787, 1 page.
Notice of Allowance in U.S. Appl. No. 16/607,459, dated Jan. 14, 2021, 23 pages.
Notice of Allowance in U.S. Appl. No. 16/607,459, dated Feb. 3, 2021, 4 pages.
Office Action in Egyptian Patent Application No. PCT529/2014, dated Dec. 7, 2020, 12 pages (with English Translation).
Office Action in U.S. Appl. No. 16/609,514, dated Dec. 9, 2020, 24 pages.
Official Notification in U.S. Appl. No. 16/607,459, dated Mar. 2, 2021, 2 pages.
Schuck et al., "Population pharmacokinetic-pharmacodynamic (PPK/PD) modeling of E2027, a selective phosphodiesterase-9 (PDE9) inhibitor, following single ascending oral doses in healthy volunteers," Poster presented at Alzheimer's Association International Conference (AAIC), Jul. 16-20, 2017, Pl-056, 1 page.
Search Report in European Patent Application No. 18808870.2, dated Feb. 17, 2021, 4 pages.
Search Report in European Patent Application No. 18809656.4, dated Jan. 22, 2021, 7 pages.
Search Report in European Patent Application No. 18810578.7, dated Jan. 20, 2021, 6 pages.
Submission Document in Egyptian Patent Application No. PCT529/2014, dated Mar. 4, 2021, 12 pages (with English Translation).
Submission Document in U.S. Appl. No. 16/607,459, dated Feb. 23, 2021, 18 pages.
Submission Document in U.S. Appl. No. 16/609,514, dated Mar. 9, 2021, 13 pages.
Notice of Allowance in Australian Patent Application No. 2014250392, dated Feb. 14, 2018, 3 pages.
Notice of Allowance in Canadian Patent Application No. 2861795, dated Sep. 7, 2018, 1 page (with English Translation).
Notice of Allowance in Canadian Patent Application No. 2907971, dated Sep. 1, 2020, 1 page (with English Translation).
Notice of Allowance in Chinese Patent Application No. 201280046653.2, dated Jun. 23, 2015, 4 pages (with English Translation).
Notice of Allowance in Chinese Patent Application No. 201480017423.2, dated Mar. 20, 2017, 4 pages (with English Translation).
Notice of Allowance in Colombian Patent Application No. 14-059034, dated Aug. 18, 2015, 6 pages (with English Translation).
Notice of Allowance in European Patent Application No. 12837953.4, dated Aug. 26, 2015, 156 pages.
Notice of Allowance in European Patent Application No. 14780139.3, dated Apr. 6, 2017, 62 pages.
Notice of Allowance in Indonesian Patent Application No. P00201401905, dated Mar. 25, 2019, 5 pages (with English Translation).
Notice of Allowance in Korean Patent Application No. 10-2014-7008769, dated Dec. 3, 2018, 4 pages (with English Translation).

(56) References Cited

OTHER PUBLICATIONS

Notice of Allowance in Korean Patent Application No. 10-2015-7026005, dated May 1, 2019, 6 pages (with English Translation).
Notice of Allowance in Mexican Patent Application No. MX/a/2014/003 800, dated Jun. 22, 2018, 4 pages (with English Translation).
Notice of Allowance in Mexican Patent Application No. MX/a/2015/013620, dated Sep. 18, 2018, 5 pages (with English Translation).
Notice of Allowance in Pakistani Patent Application No. 458/2016, dated Mar. 19, 2020, 1 page.
Notice of Allowance in Pakistani Patent Application No. 672/2012, dated Mar. 19, 2020, 1 page.
Notice of Allowance in Singaporean Patent Application No. 11201507897S, dated Oct. 27, 2017, 5 pages.
Notice of Allowance in Thai Patent Application No. 1401001864, dated Sep. 26, 2019, 2 pages (with English Translation).
Notice of Allowance in U.S. Appl. No. 14/778,695, dated Nov. 4, 2016, 9 pages.
Office Action in Canadian Patent Application No. 2861795, dated May 30, 2018, 3 pages.
Office Action in Canadian Patent Application No. 2907971, dated Apr. 28, 2020, 5 pages.
Office Action in Indian Patent Application No. 2463/CHENP/2014, dated Jun. 11, 2018, 6 pages (with English Translation).
Office Action in Indian Patent Application No. 5808/CHENP/2015, dated Oct. 26, 2018, 5 pages (with English Translation).
Office Action in Indian Patent Application No. 5808/CHENP/2015, dated May 28, 2019, 2 pages (with English Translation).
Office Action in Indonesian Patent Application No. P00201401905, dated Nov. 26, 2018, 5 pages (with English Translation).
Office Action in Israeli Patent Application No. 241796, dated Feb. 14, 2018, 8 pages (with English Translation).
Office Action in Korean Patent Application No. 10-2014-7008769, dated Sep. 3, 2018, 8 pages (with English Translation).
Office Action in Korean Patent Application No. 10-2015-7026005, dated Jan. 2, 2019, 10 pages (with English Translation).
Office Action in Malaysian Patent Application No. PI2014700702, dated Jun. 29, 2018, 3 pages.
Office Action in Mexican Patent Application No. MX/a/2014/003800, dated Jan. 15, 2018, 9 pages (with English Translation).
Office Action in Mexican Patent Application No. MX/a/2015/013620, dated May 22, 2018, 13 pages (with English Translation).
Office Action in Pakistani Patent Application No. 458/2016, dated Apr. 6, 2018, 2 pages.
Submission Document in Canadian Patent Application No. 2861795, dated Jul. 17, 2018, 12 pages.
Submission Document in Canadian Patent Application No. 2907971, dated Jun. 26, 2020, 12 pages.
Submission Document in Indian Patent Application No. 2463/CHENP/2014, dated Nov. 30, 2018, 10 pages.
Submission Document in Indian Patent Application No. 5808/CHENP/2015, dated Jan. 16, 2019, 6 pages.
Submission Document in Indian Patent Application No. 5808/CHENP/2015, dated Jul. 2, 2019, 88 pages.
Submission Document in Indonesian Patent Application No. P00201401905, dated Feb. 22, 2019, 7 pages (with English Translation).
Submission Document in Israeli Patent Application No. 241796, dated Jun. 3, 2018, 3 pages (with English Translation).
Submission Document in Korean Patent Application No. 10-2014-7008769, dated Oct. 1, 2018, 11 pages (with English Translation).
Submission Document in Korean Patent Application No. 10-2015-7026005, dated Feb. 14, 2019, 23 pages (with English Translation).
Submission Document in Mexican Patent Application No. MX/a/2014/003800, dated Feb. 16, 2018, 4 pages (with English Translation).
Submission Document in Mexican Patent Application No. MX/a/2015/013620, dated Jun. 25, 2018, 8 pages (with English Translation).
Submission Document in Pakistani Patent Application No. 458/2016, dated Jul. 2, 2018, 3 pages.
Submission Document in Pakistani Patent Application No. 458/2016, dated May 29, 2020, 8 pages.
Office Action in Australian Patent Application No. 2018278422, dated Jul. 7, 2021, 3 pages.
Doose et al., "Single-Dose Pharmacokinetics and Effect of Food on the Bioavailability of Topiramate, A Novel Antiepileptic Drug," The Journal of Clinical Pharmacology, 1996, 36:884-891.
Notice of Allowance in Russian Patent Application No. 2015140619, dated Apr. 20, 2021, 12 pages (with English Translation).
Notice of Allowance in U.S. Appl. No. 16/607,459, dated May 18, 2021, 15 pages.
Notice of Allowance in Vietnamese Patent Application No. 1-2014-01049, dated Jul. 31, 2017, 2 pages (with English Translation).
Office Action in Argentine Patent Application No. P120103702, dated Aug. 16, 2019, 4 pages (with English Translation).
Office Action in Argentine Patent Application No. P120103702, dated Apr. 20, 2021, 11 pages (with English Translation).
Office Action in Brazilian Patent Application No. BR112014007912-9, dated Jul. 2, 2019, 10 pages (with English Translation).
Office Action in Brazilian Patent Application No. BR112015024393-2, dated Oct. 22, 2019, 10 pages (with English Translation).
Office Action in Indian Patent Application No. 201947044330, dated Jun. 14, 2021, 5 pages (with English Translation).
Office Action in Indian Patent Application No. 201947044352, dated Jun. 25, 2021, 6 pages (with English Translation).
Office Action in Indian Patent Application No. 201947044546, dated May 5, 2021, 5 pages (with English Translation).
Office Action in Indian Patent Application No. 201947044589, dated Jun. 29, 2021, 6 pages (with English Translation).
Office Action in Mexican Patent Application No. MX/a/2019/013198, dated Mar. 18, 2021, 8 pages (with English Translation).
Office Action in Peruvian Patent Application No. 000408-2014, dated Mar. 12, 2018, 13 pages (with English Translation).
Office Action in Russian Patent Application No. 2015140619, dated Mar. 26, 2018, 12 pages (with English Translation).
Office Action in U.S. Appl. No. 16/609,514, dated Jun. 8, 2021, 26 pages.
Office Action in U.S. Appl. No. 16/611,374. dated May 12, 2021, 34 pages.
Office Action in Vietnamese Patent Application No. 1-2014-01049, dated May 15, 2014, 2 pages (with English Translation).
Office Action in Vietnamese Patent Application No. 1-2014-01049, dated May 16, 2017, 2 pages (with English Translation).
Submission Document in Argentine Patent Application No. P120103702, dated Oct. 24, 2019, 10 pages (with English Translation).
Submission Document in Argentine Patent Application No. P120103702, dated Jul. 5, 2021, 357 pages (with English Translation).
Submission Document in Brazilian Patent Application No. BR112014007912-9, dated Aug. 26, 2019, 12 pages (with English Translation).
Submission Document in Brazilian Patent Application No. BR112015024393-2, dated Jan. 17, 2020, 18 pages (with English Translation).
Submission Document in European Patent Application No. 18810202.4, dated Jun. 14, 2021, 23 pages.
Submission Document in Peruvian Patent Application No. 000408-2014, dated Apr. 10, 2018, 14 pages (with English Translation).
Submission Document in Russian Patent Application No. 2015140619, dated Apr. 10, 2018, 12 pages (with English Translation).
Submission Document in Vietnamese Patent Application No. 1-2014-01049, dated Jun. 12, 2014, 19 pages (with English Translation).
Submission Document in Vietnamese Patent Application No. 1-2014-01049, dated Jun. 8, 2017, 11 pages (with English Translation).
Tandfonline.com [online], Vardigan et al., "The Selective Phosphodiesterase 9 (PDE9) Inhibitor PF-04447943 Attenuates a Scopolamine-Induced Deficit in a Novel Rodent Attention Task," Abstract, Journal of Neurogenetics, Nov. 2011, 25(4), [Retrieved on May 7, 2021], retrieved from: URL<https://doi.org/10.3109/01677063,2011,630494>, 2 pages.
Notice of Allowance in U.S. Appl. No. 16/607,459, dated Jul. 30, 2021, 5 pages.

(56) References Cited

OTHER PUBLICATIONS

Notice of Allowance in U.S. Appl. No. 16/607,459, dated Aug. 19, 2021, 5 pages.
Office Action in Mexican Patent Application No. MX/a/2019/013383, dated Aug. 17, 2021, 8 pages (with English Translation).
Office Action in Russian Patent Application No. 2019135690, dated Aug. 25, 2021, 24 pages (with English Translation).
Submission Document in European Patent Application No. 18808870.2, dated Sep. 9, 2021, 9 pages.
Submission Document in European Patent Application No. 18809656.4, dated Aug. 19, 2021, 9 pages.
Submission Document in European Patent Application No. 18810578.7, dated Aug. 16, 2021, 13 pages.
Submission Document in Mexican Patent Application No. MX/a/2019/013198, dated Jul. 21, 2021, 11 pages (with English Translation).
Submission Document in U.S. Appl. No. 16/607,459, dated Aug. 13, 2021, 12 pages.
Office Action in European Patent Application No. 18810202.4, dated Nov. 15, 2021, 7 pages.
Notice of Allowance in U.S. Appl. No. 16/611,374, dated Dec. 1, 2021, 8 pages.
Submission Document in U.S. Appl. No. 16/611,374, dated Nov. 9, 2021, 18 pages.
Office Action in Taiwanese Patent Application No. 107118423, dated Dec. 23, 2021, 9 pages (with English Translation).
Submission Document in Mexican Patent Application No. MX/a/2019/013397, dated Jan. 13, 2022, 9 pages (with English Translation).
Office Action in Mexican Patent Application No. MX/a/2019/013397, dated Feb. 2, 2022, 15 pages (with English Translation).
Submission Document in Australian Patent Application No. 2018278422, dated Feb. 21, 2022, 10 pages
Office Action in Brazilian Patent Application No. BR1120190235523, dated Aug. 2, 2022, 9 pages (with English Translation).
Submission Document in Russian Patent Application No. 2019135690, dated Sep. 26, 2022, 15 pages (with English Translation).
Darpo et al., "ECG Evaluation as Part of the Clinical Pharmacology Strategy in the Development of New Drugs: A Review of Current Practices and Opportunities Based on Five Case Studies," The Journal of Clinical Pharrnacolog, 2022, 62(12):1480-1500.
Irizarry et al., "OC02—Results of a Phase 2/3 Placebo-Controlled, Double-Blind, Parallel-Group, Randomized Study to Evaluate the Efficacy and Safety of 12 Week Treatment with the Phosphodiesterase 9 (PDE9) Inhibitor Irsenontrine (E2027) in Subjects With Dementia With Lewy Bodies," Abstract, 15th Clinical Trials on Alzheimer's Disease Conference, San Francisco, CA, USA, Nov. 29-Dec. 2, 2022, p. S13.
Irizarry et al., "Results of a Phase 2/3 Placebo-Controlled, Double-Blind, Parallel-Group, Randomized Study to Evaluate the Efficacy and Safety of 12 Week Treatment with the Phosphodiesterase 9 (PDE9) Inhibitor Irsenontrine (E2027) in Subjects With Dementia With Lewy Bodies," Presentation Slides, 2022 Clinical Trials on Alzheimer's Disease Annual Meeting, 2022, 13 pages.
Kharkevich "Educational Literature—For students of medical institutes," 3rd Ed., Approved by the Main Directorate of Educational Institutions of the Ministry of Health of the USSR, Moscow "Medicine" 1987, Pharmacology, 1987, 6 pages (with English Translation).
Kharkevich, "Farmakologiya [Pharmacology]," 10th ed., GEOTAR-Media, 2010, 908, pp. 72-82 (with Full Translation).
Landry et al., "E2027 Cardiac Safety Evaluation With Concentration-Response Modeling of ECG Data to Inform Dose Selection in Studies in Patients With Dementia With Lewy Bodies," Alzheimer Disease & Associated Disorders, 2022, 36(3):208-214.
lsgeotarru [Online], "The Internet source of the GEOTAR Medicinal Handbook—Alzepil®," available on or before Mar. 3, 2018, via Internet Archive: Wayback Machine URL<https://web.archive.org/web/20180303154442/http://www.lsgeotarru:80/alzepil-296.html>, retrieved on or before Jan. 23, 2023, URL<http://www.lsgeotar.ru/alzepil-296.html>, 11 pages (with English Translation).
Mashkovsky, "Lekarstvennye sredstva [Medicaments]—Manual for Physicians—vol. 1," 14th Ed, revised, modified, and supplemented, Moscow, LLC "Novaya Volna", S.B. Divov, 2002, 10 pages (with English Translation).
Nekrasov et al., "Mental Disorders of Late Age," Medical Education: Department of Psychiatry and Narcology, Mechnikov Publishing House of NWSMU, 2015, 7 pages (with English Translation).
Office Action in Chinese Patent Application No. 201880030146.7, dated Jan. 5, 2023, 7 pages (with English Translation).
Office Action in European Patent Application No. 18810202.4, dated Nov. 8, 2022, 9 pages.
Office Action in Japanese Patent Application No. P2019-521251, dated Dec. 6, 2022, 8 pages (with English Translation).
Office Action in Russian Patent Application No. 2019135690, dated Nov. 23, 2022, 15 pages (with English Translation).
Office Action in Russian Patent Application No. 2019135834, dated Dec. 28, 2022, 14 pages (with English Translation).
Sachdev et al., "The Effects of the Novel Phosphodiesterase 9 (PDE9) Inhibitor E2027 (Iresnontrine) on CSF Cyclic Guanosine Monophosphase (CGMP), Additional CSF and Plasma Biomarkers, and Clinical Outcomes in Amyloid Positive and Amyloid Negative Patients with Dementia with Lewy Bodies (DLB) and Parkinson's Disease Dementia (PDD)," Poster Presentation, Poster Board No. P048, Presented at the 2022 Clinical Trials on Alzheimer's Disease Annual Meeting (CTAD 2022), Nov. 29-Dec. 2, 2022, San Francisco, CA, USA, Eisai Inc., 1 page.
Submission Document in Brazilian Patent Application No. BR1120190235698, dated Oct. 27, 2022, 6 pages (with English Translation).
Submission Document in Brazilian Patent Application No. BR1120190235523, dated Oct. 27, 2022, 20 pages (with English Translation).
Submission Document in Chinese Patent Application No. 201880030146.7, dated Oct. 28, 2022, 20 pages (with English Translation).
Submission Document in Chinese Patent Application No. 201880030220.5, dated Oct. 8, 2022, 81 pages (with English Translation).
Submission Document in Israeli Patent Application No. 270357, dated Nov. 13, 2022, 9 pages.
Zhulenko et al., "Pharmacology," Approved by the Ministry of Agriculture of the Russian Federation, KolosS, 2008, 511, pp. 34-35 (with English Translation).
Office Action in Brazilian Patent Application No. BR1120190235698, dated Aug. 2, 2022, 10 pages (with English Translation).
Office Action in Brazilian Patent Application No. BR112015024393-2, dated Jan. 31, 2023, 6 pages (with English Translation).
Official Notification in European Patent Application No. 18810202.4, dated Feb. 20, 2023, 4 pages.
[NO AUTHOR LISTED], "Results of a Phase 2/3 Placebo-Controlled, Double-Blind, Parallel-Group, Randomized Study to Evaluate the Efficacy of 12 Week Treatment with (S)-7-(2-Methoxy-3,5- dimethylpynridin-4-yl)-1-(tetrahydrofuran-3-yl)- 1H-pyrazolo[4,3-c]quinolin-4(5H)-one (E2027, Compound (I)) in Subjects With Dementia With Lewy Bodies (DLB)", 2023, 3 pages
Heckman et al., "Phosphodiesterase inhibitors as a target for cognition enhancement in aging and Alzheimer's disease: a translational overview," Current Pharmaceutical Design, 2015, 21:317-331.
Notice of Allowance in European Patent Application No. 18810202.4, dated Mar. 20, 2023, 20 pages.
Official Notification in European Patent Application No. 18810202.4, dated Mar. 6, 2023, 1 page.
Submission Document in Chinese Patent Application No. 201880027744.9, dated May 18, 2023, 16 pages (with English Translation).
Submission Document in Chinese Patent Application No. 201880030146.7, dated Apr. 17, 2023, 21 pages (with English Translation).
Submission Document in European Patent Application No. 18810202.4, dated Mar. 1, 2023, 24 pages.

(56) References Cited

OTHER PUBLICATIONS

Submission Document in European Patent Application No. 18810202.4, dated Feb. 14, 2023, 7 pages.
Notice before Acceptance in Israeli Patent Application No. 270357, dated Jun. 26, 2023, 3 pages.
Notice of Allowance in Russian Patent Application No. 2019135690, dated Jul. 3, 2023, 12 pages (with English Translation).
Office Action in Australian Patent Application No. 2018276565, dated Jul. 19, 2023, 10 pages.
Office Action in Korean Patent Application No. KR 10-2019-7033124, dated Aug. 1, 2023, 9 pages (with English Translation).
Submission Document in Russian Patent Application No. 2019135690, dated May 22, 2023, 24 pages (with English Translation).

\* cited by examiner

DEMENTIA THERAPEUTIC AGENT COMBINING PYRAZOLOQUINOLINE DERIVATIVE AND DONEPEZIL

TECHNICAL FIELD

The present invention relates to a therapeutic agent for dementia combining a pyrazoloquinoline derivative having phosphodiesterase 9 (PDE9) inhibitory action or a pharmaceutically acceptable salt thereof, and donepezil or a pharmaceutically acceptable salt thereof.

BACKGROUND ART

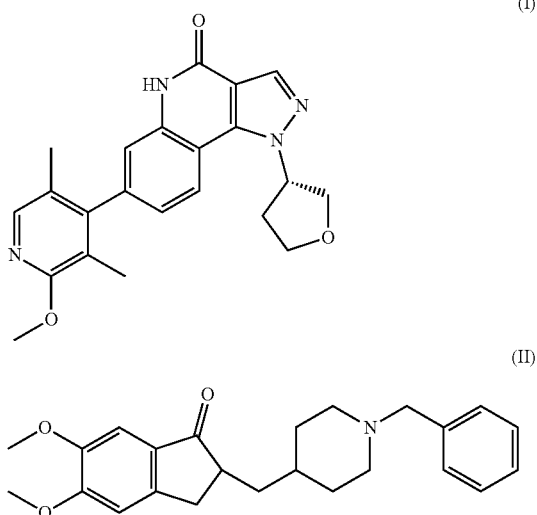

Pyrazoloquinoline derivatives represented by formula (I) (hereunder referred to as "compound (I)") have phosphodiesterase 9 (PDE9) inhibitory action, and are considered to have promising ameliorative effects on cognitive function in Alzheimer's disease (PTL 1).

Donepezil, represented by formula (II) (hereunder referred to as "compound (II)") has acetylcholine esterase-inhibitory action, and has been reported to exhibit an effect against Alzheimer's disease and Lewy body dementia (see NPLs 1, 2 and 3).

In addition, the acetylcholine esterase inhibitors galantamine and rivastigmine and the NMDA receptor antagonist memantine have been approved as therapeutic agents for Alzheimer's disease. Donepezil is indicated for mild to severe Alzheimer's disease, and has been reported to have, in addition to a cognitive function-ameliorating effect, also an effect against peripheral symptoms such as agitation, anxiety, apathy, delusion, depression, disinhibition, hallucination, irritability, aberrant motor behavior and apathy (BPSD: Behavioral and Psychological Symptoms of Dementia) (see NPLs 4 and 5). Galantamine and rivastigmine are indicated for mild to moderate Alzheimer's disease (see NPLs 6 and 7). Memantine has been reported to have efficacy for ameliorating cognitive function, and for BPSD (agitation, irritability, aggression and behavioral disorder) in moderate to severe Alzheimer's disease (see NPLs 8 and 9). Combined use of different acetylcholine esterase inhibitors is contraindicated, but any acetylcholine esterase inhibitor may be used in combination with memantine. According to the 2010 Dementia Disease Treatment Guidelines, acetylcholine esterase inhibitors are recommended for the core symptoms of Alzheimer's disease, with one of donepezil, galantamine or rivastigmine being selected first, and then switching to another acetylcholine esterase inhibitor if a problem arises in terms of effect or tolerance. When the effect of the acetylcholine esterase inhibitor is inadequate or a problem arises in terms of tolerance, combination with memantine or switching to memantine may be considered.

Acetylcholine esterase inhibitors, however, have been reported to have digestive system side-effects, and to aggravate Parkinson's symptoms (see NPL 10). In cases where acetylcholine esterase inhibitors cannot be used due to side-effects or tolerance, memantine may be selected if the patient has moderate to severe Alzheimer's disease, but at the current time no effective method of treatment exists for other patients. The combined use of acetylcholine esterase inhibitors with memantine is possible in patients that experience inadequate effects, but opinions are divided since some reports have indicated an effect by their combined use (see NPL 11) while other reports have indicated no effect (see NPL 12).

CITATION LIST

Patent Literature

[PTL 1] U.S. Pat. No. 8,563,565

Non-Patent Literature

[NPL 1] Homma et al., Dement. Geriatr. Cogn. Disord., 2000, vol. 11, p. 299
[NPL 2] Homma et al., Dement. Geriatr. Cogn. Disord., 2008, vol. 25, p. 399
[NPL 3] Mori et al., Ann. Neurol, vol. 72, p. 41 2012
[NPL 4] Holmes at al., Neurology, 2004, vol. 63, p. 214
[NPL 5] Gauthier et al., Int Psychogeriatr, 2002, vol. 14, p. 389
[NPL 6] Raskind et al., Neurology, 2000, vol. 54, p. 226
[NPL 7] Winblad et al., Neurology, 2007, vol. 69, p.S14
[NPL 8] Mecocci et al., Int J Geriatr Psychiatry, vol. 24, p. 532
[NPL 9] Grossberg et al., Dement Geriatr Cogn Disord, 2009, vol. 27, p. 164
[NPL 10] Bourke et al., Ann. Pharmacother., 1998, vol. 32, p. 610
[NPL 11] Lopez et al., J Neurol Neurosurg Psychiatry, 2009, vol. 80, p. 600
[NPL 12] Howard et al., New Eng J. Med., 2012, vol. 366, p. 893

SUMMARY OF INVENTION

Technical Problem

It is currently the case that no satisfactory method of treatment exists for Alzheimer's disease or Lewy body dementia, while an effective anti-dementia agent is also yet to be developed.

Solution to Problem

In order to solve this problem, the present inventors have carried out much ardent research using a scopolamine-induced cognitive impairment rat model, and as a result we have completed this invention upon finding that the combined use of compound (I) or a pharmaceutically acceptable salt thereof with compound (II) or a pharmaceutically acceptable salt thereof surprisingly exhibits an effect of inhibiting scopolamine-induced cognitive impairment, in doses that are ineffective with each alone.

Specifically, the invention relates to the following <1> to <19.3>.

<1> A therapeutic agent for Alzheimer's disease or Lewy body dementia, for combined use of (S)-7-(2-methoxy-3,5-dimethylpyridin-4-yl)-1-(tetrahydrofuran-3-yl)-1H-pyrazolo[4,3-c]quinoline-4(5H)-one represented by formula (I):

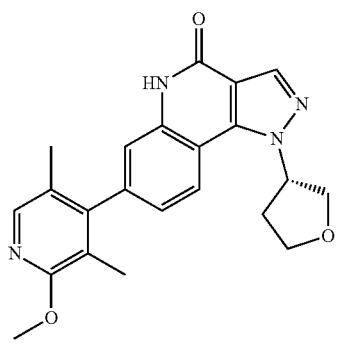

(I)

or a pharmaceutically acceptable salt thereof, and donepezil represented by formula (II):

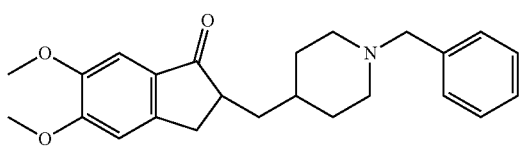

(II)

or a pharmaceutically acceptable salt thereof.

<2> The therapeutic agent according to <1>, wherein the donepezil or pharmaceutically acceptable salt thereof is donepezil hydrochloride.

<3> The therapeutic agent according to <1> or <2>, wherein the (S)-7-(2-methoxy-3,5-dimethylpyridin-4-yl)-1-(tetrahydrofuran-3-yl)-1H-pyrazolo[4,3-c]quinoline-4(5H)-one or pharmaceutically acceptable salt thereof is (S)-7-(2-methoxy-3,5-dimethylpyridin-4-yl)-1-(tetrahydrofuran-3-yl)-1H-pyrazolo[4,3-c]quinoline-4(5H)-one maleate.

<4> The therapeutic agent according to any one of <1> to <3>, wherein the Alzheimer's disease is mild, moderate or severe Alzheimer's disease.

<5> A therapeutic agent for Alzheimer's disease or Lewy body dementia for simultaneous or separate administration of (S)-7-(2-methoxy-3,5-dimethylpyridin-4-yl)-1-(tetrahydrofuran-3-yl)-1H-pyrazolo[4,3-c]quinoline-4(5H)-one represented by formula (I):

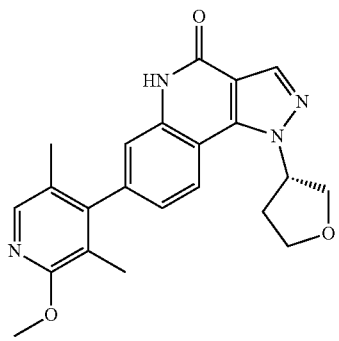

(I)

or a pharmaceutically acceptable salt thereof, and donepezil represented by formula (II):

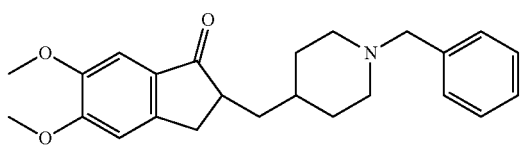

(II)

or a pharmaceutically acceptable salt thereof.

<6> The therapeutic agent according to <5>, wherein the donepezil or pharmaceutically acceptable salt thereof is donepezil hydrochloride.

<7> The therapeutic agent according to <5> or <6>, wherein the (S)-7-(2-methoxy-3,5-dimethylpyridin-4-yl)-1-(tetrahydrofuran-3-yl)-1H-pyrazolo[4,3-c]quinoline-4(5H)-one or pharmaceutically acceptable salt thereof is (S)-7-(2-methoxy-3,5-dimethylpyridin-4-yl)-1-(tetrahydrofuran-3-yl)-1H-pyrazolo[4,3-c]quinoline-4(5H)-one maleate.

<8> The therapeutic agent according to any one of <5> to <7>, wherein the Alzheimer's disease is mild, moderate or severe Alzheimer's disease.

<9> A therapeutic agent for Alzheimer's disease or Lewy body dementia, comprising (S)-7-(2-methoxy-3,5-dimethylpyridin-4-yl)-1-(tetrahydrofuran-3-yl)-1H-pyrazolo[4,3-c]quinoline-4(5H)-one represented by formula (I):

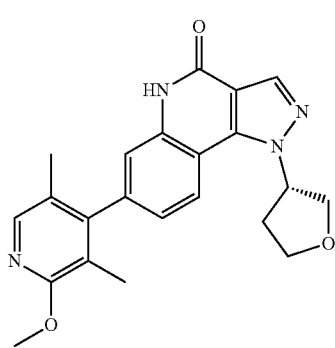

(I)

or a pharmaceutically acceptable salt thereof, and donepezil represented by formula (II):

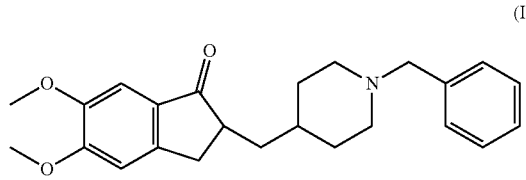
(II)

or a pharmaceutically acceptable salt thereof.
<10> The therapeutic agent according to <9>, wherein the donepezil or pharmaceutically acceptable salt thereof is donepezil hydrochloride.
<11> The therapeutic agent according to <9> or <10>, wherein the (S)-7-(2-methoxy-3,5-dimethylpyridin-4-yl)-1-(tetrahydrofuran-3-yl)-1H-pyrazolo[4,3-c]quinoline-4(5H)-one or pharmaceutically acceptable salt thereof is (S)-7-(2-methoxy-3,5-dimethylpyridin-4-yl)-1-(tetrahydrofuran-3-yl)-1H-pyrazolo[4,3-c]quinoline-4(5H)-one maleate.
<12> The therapeutic agent according to any one of <9> to <11>, wherein the Alzheimer's disease is mild, moderate or severe Alzheimer's disease.
<13> Donepezil represented by formula (II):

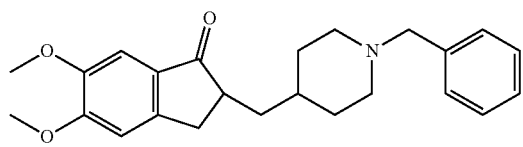
(II)

or a pharmaceutically acceptable salt thereof, for treatment of Alzheimer's disease or Lewy body dementia by use in combination with (S)-7-(2-methoxy-3,5-dimethylpyridin-4-yl)-1-(tetrahydrofuran-3-yl)-1H-pyrazolo[4,3-c]quinoline-4(5H)-one represented by formula (I):

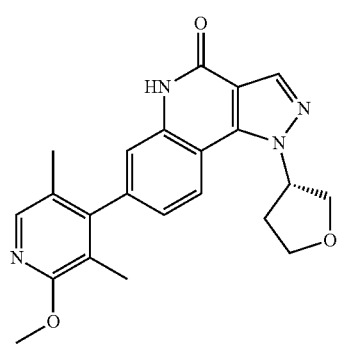
(I)

or a pharmaceutically acceptable salt thereof.
<13.1> Donepezil or a pharmaceutically acceptable salt thereof according to <13>, wherein the donepezil or pharmaceutically acceptable salt thereof is donepezil hydrochloride.
<13.2> Donepezil or a pharmaceutically acceptable salt thereof according to <13> or <13.1>, wherein the (S)-7-(2-methoxy-3,5-dimethylpyridin-4-yl)-1-(tetrahydrofuran-3-yl)-1H-pyrazolo[4,3-c]quinoline-4(5H)-one or pharmaceutically acceptable salt thereof is (S)-7-(2-methoxy-3,5-dimethylpyridin-4-yl)-1-(tetrahydrofuran-3-yl)-1H-pyrazolo[4,3-c]quinoline-4(5H)-one maleate.
<13.3> Donepezil or a pharmaceutically acceptable salt thereof according to any one of <13> to <13.2>, wherein the Alzheimer's disease is mild, moderate or severe Alzheimer's disease.
<14> (S)-7-(2-methoxy-3,5-dimethylpyridin-4-yl)-1-(tetrahydrofuran-3-yl)-1H-pyrazolo[4,3-c]quinoline-4(5H)-one represented by formula (I):

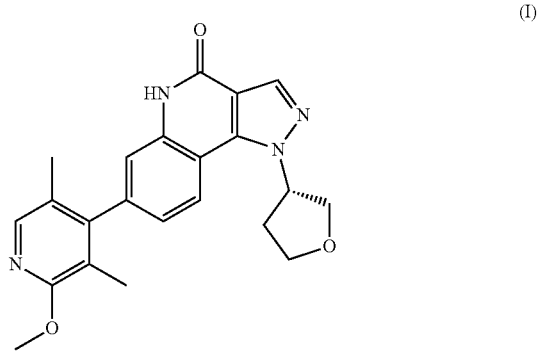
(I)

or a pharmaceutically acceptable salt thereof, for treatment of Alzheimer's disease or Lewy body dementia by use in combination with donepezil represented by formula (II):

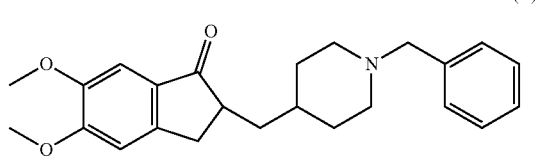
(II)

or a pharmaceutically acceptable salt thereof.
<14.1> A compound represented by formula (I) or a pharmaceutically acceptable salt thereof according to <14>, wherein the donepezil or pharmaceutically acceptable salt thereof is donepezil hydrochloride.
<14.2> A compound represented by formula (I) or a pharmaceutically acceptable salt thereof according to <14> or <14.1>, wherein the (S)-7-(2-methoxy-3,5-dimethylpyridin-4-yl)-1-(tetrahydrofuran-3-yl)-1H-pyrazolo[4,3-c]quinoline-4(5H)-one or pharmaceutically acceptable salt thereof is (S)-7-(2-methoxy-3,5-dimethylpyridin-4-yl)-1-(tetrahydrofuran-3-yl)-1H-pyrazolo[4,3-c]quinoline-4(5H)-one maleate.
<14.3> A compound represented by formula (I) or a pharmaceutically acceptable salt thereof according to any one of <14> to <14.2>, wherein the Alzheimer's disease is mild, moderate or severe Alzheimer's disease.

<15> A method for treating Alzheimer's disease or Lewy body dementia for combined use of (S)-7-(2-methoxy-3,5-dimethylpyridin-4-yl)-1-(tetrahydrofuran-3-yl)-1H-pyrazolo[4,3-c]quinoline-4(5H)-one represented by formula (I):

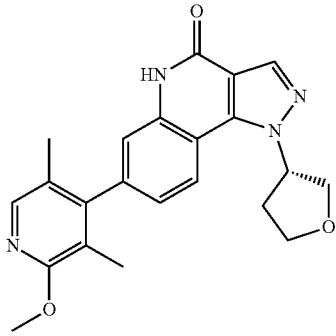

(I)

or a pharmaceutically acceptable salt thereof, and donepezil represented by formula (II):

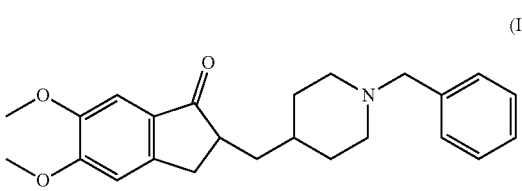

(II)

or a pharmaceutically acceptable salt thereof.

<15.1> The method according to <15>, wherein the donepezil or pharmaceutically acceptable salt thereof is donepezil hydrochloride.

<15.2> The method according to <15> or <15.1>, wherein the (S)-7-(2-methoxy-3,5-dimethylpyridin-4-yl)-1-(tetrahydrofuran-3-yl)-1H-pyrazolo[4,3-c]quinoline-4(5H)-one or pharmaceutically acceptable salt thereof is (S)-7-(2-methoxy-3,5-dimethylpyridin-4-yl)-1-(tetrahydrofuran-3-yl)-1H-pyrazolo[4,3-c]quinoline-4(5H)-one maleate.

<15.3> The method according to any one of <15> to <15.2>, wherein the Alzheimer's disease is mild, moderate or severe Alzheimer's disease.

<16> A pharmaceutical composition comprising (S)-7-(2-methoxy-3,5-dimethylpyridin-4-yl)-1-(tetrahydrofuran-3-yl)-1H-pyrazolo[4,3-c]quinoline-4(5H)-one represented by formula (I):

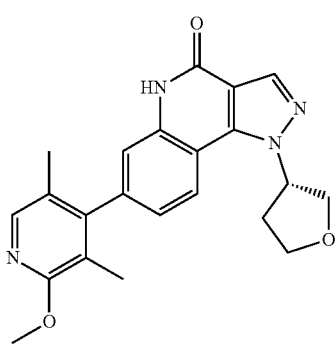

(I)

or a pharmaceutically acceptable salt thereof, donepezil represented by formula (II):

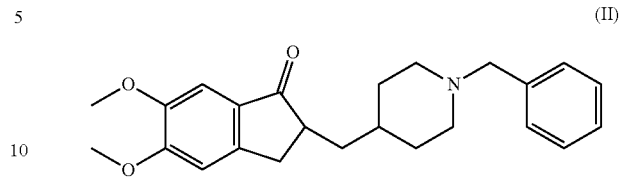

(II)

or a pharmaceutically acceptable salt thereof, and an excipient.

<16.1> The pharmaceutical composition according to <16>, wherein the donepezil or pharmaceutically acceptable salt thereof is donepezil hydrochloride.

<16.2> The pharmaceutical composition according to <16> or <16.1>, wherein the (S)-7-(2-methoxy-3,5-dimethylpyridin-4-yl)-1-(tetrahydrofuran-3-yl)-1H-pyrazolo[4,3-c]quinoline-4(5H)-one or pharmaceutically acceptable salt thereof is (S)-7-(2-methoxy-3,5-dimethylpyridin-4-yl)-1-(tetrahydrofuran-3-yl)-1H-pyrazolo[4,3-c]quinoline-4(5H)-one maleate.

<17> A kit comprising:
a pharmaceutical composition comprising (S)-7-(2-methoxy-3,5-dimethylpyridin-4-yl)-1-(tetrahydrofuran-3-yl)-1H-pyrazolo[4,3-c]quinoline-4(5H)-one represented by formula (I):

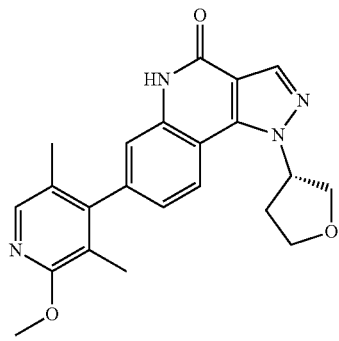

(I)

or a pharmaceutically acceptable salt thereof, and an excipient, and
a pharmaceutical composition comprising donepezil represented by formula (II):

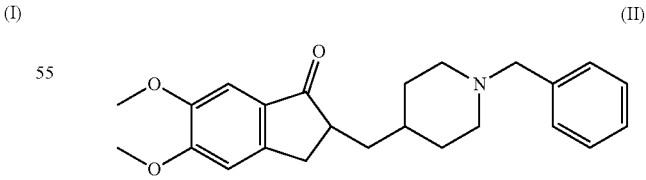

(II)

or a pharmaceutically acceptable salt thereof, and an excipient.

<17.1> The kit according to <17>, wherein the donepezil or pharmaceutically acceptable salt thereof is donepezil hydrochloride.

<17.2> The kit according to <17> or <17.1>, wherein the (S)-7-(2-methoxy-3,5-dimethylpyridin-4-yl)-1-(tetrahydrofuran-3-yl)-1H-pyrazolo[4,3-c]quinoline-4(5H)-one or pharmaceutically acceptable salt thereof is (S)-7-(2-methoxy-3,5-dimethylpyridin-4-yl)-1-(tetrahydrofuran-3-yl)-1H-pyrazolo[4,3-c]quinoline-4(5H)-one maleate.

<18> The use of donepezil represented by formula (II):

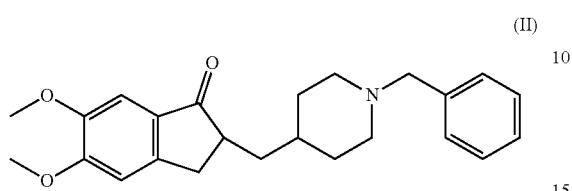

(II)

or a pharmaceutically acceptable salt thereof, for production of a therapeutic agent for Alzheimer's disease or Lewy body dementia by use in combination with (S)-7-(2-methoxy-3,5-dimethylpyridin-4-yl)-1-(tetrahydrofuran-3-yl)-1H-pyrazolo[4,3-c]quinoline-4(5H)-one represented by formula (I):

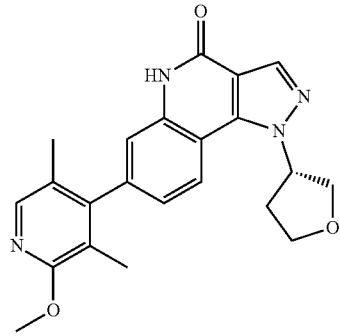

(I)

or a pharmaceutically acceptable salt thereof.

<18.1> The use of donepezil or a pharmaceutically acceptable salt thereof according to <18>, wherein the donepezil or pharmaceutically acceptable salt thereof is donepezil hydrochloride.

<18.2> The use of donepezil or a pharmaceutically acceptable salt thereof according to <18> or <18.1>, wherein the (S)-7-(2-methoxy-3,5-dimethylpyridin-4-yl)-1-(tetrahydrofuran-3-yl)-1H-pyrazolo[4,3-c]quinoline-4(5H)-one or pharmaceutically acceptable salt thereof is (S)-7-(2-methoxy-3,5-dimethylpyridin-4-yl)-1-(tetrahydrofuran-3-yl)-1H-pyrazolo[4,3-c]quinoline-4(5H)-one maleate.

<18.3> The use of donepezil or a pharmaceutically acceptable salt thereof according to any one of <18> to <18.2>, wherein the Alzheimer's disease is mild, moderate or severe Alzheimer's disease.

<19> The use of (S)-7-(2-methoxy-3,5-dimethylpyridin-4-yl)-1-(tetrahydrofuran-3-yl)-1H-pyrazolo[4,3-c]quinoline-4(5H)-one represented by formula (I):

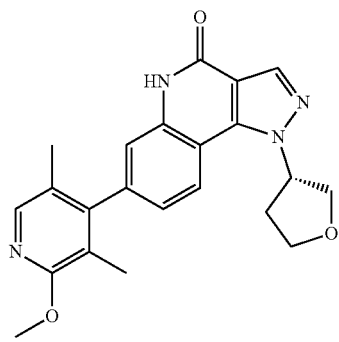

(I)

or a pharmaceutically acceptable salt thereof, for production of a therapeutic agent for Alzheimer's disease or Lewy body dementia by use in combination with donepezil represented by formula (II):

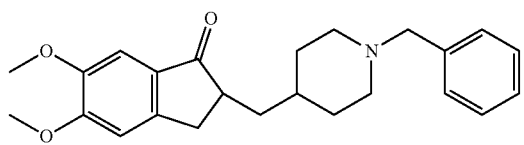

(II)

or a pharmaceutically acceptable salt thereof.

<19.1> The use of a compound represented by formula (I) or a pharmaceutically acceptable salt thereof according to <19>, wherein the donepezil or pharmaceutically acceptable salt thereof is donepezil hydrochloride.

<19.2> The use of a compound represented by formula (I) or a pharmaceutically acceptable salt thereof according to <19> or <19.1>, wherein the (S)-7-(2-methoxy-3,5-dimethylpyridin-4-yl)-1-(tetrahydrofuran-3-yl)-1H-pyrazolo[4,3-c]quinoline-4(5H)-one or pharmaceutically acceptable salt thereof is (S)-7-(2-methoxy-3,5-dimethylpyridin-4-yl)-1-(tetrahydrofuran-3-yl)-1H-pyrazolo[4,3-c]quinoline-4(5H)-one maleate.

<19.3> The use of a compound represented by formula (I) or a pharmaceutically acceptable salt thereof according to any one of <19> to <19.2>, wherein the Alzheimer's disease is mild, moderate or severe Alzheimer's disease.

Advantageous Effects of Invention

The present invention provides a therapeutic agent for Alzheimer's disease and Lewy body dementia, combining a pyrazoloquinoline derivative represented by formula (I) having PDE9 inhibitory action, or a pharmaceutically acceptable salt thereof, and donepezil having acetylcholine esterase inhibitory action, or a pharmaceutically acceptable salt thereof. The therapeutic agent using this combination exhibits a more notable ameliorative effect on cognitive function in animal models compared to their uses alone, and it has potential for use as a therapeutic agent for Alzheimer's disease and Lewy body dementia.

DESCRIPTION OF EMBODIMENTS

The present invention will now be explained in detail.
A "pharmaceutically acceptable salt" as referred to throughout the present specification is not particularly limited as long as it is a salt formed with the compound of the invention, and specific examples include acid addition salts such as inorganic acid salts, organic acid salts or acidic amino acid salts.

Unless otherwise specified, in the context of "pharmaceutically acceptable salt" as used herein, the number of acid molecules per one molecule of the compound in a formed salt is not particularly limited as long as the salt is formed in an appropriate ratio. In one embodiment, the number of acid molecules per one molecule of the compound is about 0.1 to about 5; in another embodiment, the number of acid molecules per one molecule of the compound is about 0.5 to about 2; and in still another embodiment, the number of acid molecules per one molecule of the compound is about 0.5, about 1 or about 2.

Specific examples of an inorganic acid salt include hydrochloride, hydrobromide, sulfate, nitrate and phosphate, and specific examples of an organic acid salt include acetate, succinate, fumarate, maleate, tartrate, citrate, lactate, stearate, benzoate, methanesulfonate, p-toluenesulfonate and benzenesulfonate.

Specific examples of an acidic amino acid salt include aspartate and glutamate.

[Formulation]

The pharmaceutical composition of the invention can be produced by mixing a pharmaceutically acceptable additive with compound (I) or a pharmaceutically acceptable salt thereof, and/or compound (II) or a pharmaceutically acceptable salt thereof. The pharmaceutical composition of the invention can be produced by a known method, such as the method described in the General Rules for Preparations of the Japanese Pharmacopoeia, 16th Edition.

The pharmaceutical composition of the invention can be appropriately administered to a patient according to the dosage form.

The dose of compound (I) or a pharmaceutically acceptable salt thereof and compound (II) or a pharmaceutically acceptable salt thereof according to the invention will vary depending on the severity of symptoms, the patient age, gender and body weight, the form of administration and type of salt, and the specific type of disease, and the like; but usually, in adult, about 30 µg to 10 g, in one embodiment 100 µg to 5 g, and in another embodiment 100 µg to 1 g is administered orally per day, in a single dose or in several divided doses; or about 30 µg to 1 g, in one embodiment 100 µg to 500 mg, and in another embodiment 100 µg to 300 mg is administered by injection per day, in a single dose or in several divided doses.

EXAMPLES

Compound (I) can be produced by the method described in PTL 1, for example.

Pharmacological Test Examples

The present inventors confirmed the combined effects of compound (I) and donepezil hydrochloride using the following animal model.

[Test Example 1] Novel Object Recognition Test Using Rats with Scopolamine-Induced Cognitive Impairment Acetylcholine nervous system disorder has been reported in Alzheimer's disease and Lewy body dementia (Whitehouse et al., Science, 1982, vol. 215, p. 1237, Shimada et al., Neurology, vol. 73, p. 273, 2009, Tiraboschi et al., Neurology 54 (2000) 407-411, Peny et. al., NeuroReport, vol. 5, pp. 747-749 (1994)), and scopolamine-administered animals are utilizable as an animal model for Alzheimer's disease and Lewy body dementia.

Scopolamine is a muscarine receptor inhibitor which blocks acetylcholine nervous system transmission. The acetylcholine nervous system is involved in memory and attention, and healthy humans or animals administered scopolamine exhibit dementia-like amnesia symptoms which are attenuated by drugs used for treatment of cognitive impairment in Alzheimer's disease and Lewy body dementia (Snyder et al., Alzheimer's & Dementia 1 (2005) 126-135, Sambeth et al., European Journal of Pharmacology, vol. 572 (2007) pp. 151-159).

Materials and Methods 6-week-old male Long Evans rats (Institute for Animal Reproduction) were subjected to the test. A habituation process to the experimental procedure was carried out once per day for 2 days prior to the test. In the habituation process, a vehicle was administered to the rats, and then the rats were placed in an empty test apparatus (40 cm×30 cm×45 cm height) and allowed to explore for 3 minutes, and after then placed in a waiting chamber (13 cm×30 cm×45 cm height) for about 1 minute, they were returned to the empty test apparatus again and left for 5 minutes.

An acquisition trial (T1) was carried out on the day of the test. Compound (I) was orally administered 2 hours before T1. Donepezil hydrochloride was orally administered 1 hour before T1. Scopolamine (Wako Pure Chemical Industries, Ltd.) was subcutaneously administered 30 minutes before T1 at a dose of 0.7 mg/kg. In T1, the rats were habituated to the empty test apparatus for 3 minutes and then placed in the waiting chamber. After setting two identical objects in the test apparatus, the rats were returned into the test apparatus again and allowed to freely explore the two identical objects for 5 minutes. The rats were then returned into their rearing cages. After 2 hours, a retention trial (T2) was carried out. The rats were placed in the empty test apparatus for 3 minutes for habituation, and were then transferred into the waiting chamber. After setting an object used in T1 ("familiar" object) and an object not used in T1 ("novel" object) in the test apparatus, the rats were again returned into the test apparatus and allowed to freely explore these objects for 3 minutes. The objects were wiped with a wet wipe impregnated with ethanol after each experiment so as to leave no trace of odor. The behaviors of the rats during T1 and T2 were recorded by a digital video camera, and the total exploration time for each object was manually measured using a stopwatch. Exploratory behavior was defined as the behavior in which the rat brings its nose within 2 cm of the object and directs its nose toward the object.

In the novel object recognition test, the percentage of exploration of the novel object in T2 is considered to be an index for amnesia, reflecting discrimination between the familiar object and the novel object. The percentage of exploration of the novel object was calculated by the following formula.

$$\text{The percentage of exploration of the novel object } (\%) = N/(N+F) \times 100$$

F: time spent in exploring the familiar object

N: time spent in exploring the novel object

Rats whose total time spent in exploring the objects during T1 or T2 was 10 seconds or less or rats whose percentage of the time spent in exploring either of the objects during T1 was not less than 70% or not more than 30% of the total exploration time were excluded from the data analysis.

The results were expressed as mean±standard error. The difference between the normal control group untreated with scopolamine and the disease control group treated with scopolamine was analyzed by an unpaired t-test (significant difference: *). The difference between the disease control group and the single drug-treated group was analyzed by Dunnett-type multiple comparison test (significant difference: #). The difference between the combined treatment group and the single drug-treated group was analyzed by Dunnett-type multiple comparison test (significant difference: ✕). A value of $p<0.05$ was judged to be a statistically significant difference. Statistical analysis was conducted using GraphPad Prism version 5.04 or 6.02. The results are shown in Tables 1 to 5.

TABLE 1

| | Scopolamine-administered group | | |
|---|---|---|---|
| Normal control group | Disease control group | Compound (I) 0.3 mg/kg | Compound (I) 1 mg/kg |
| 71.3 ± 3.1 | 54.4 ± 2.8* | 58.7 ± 3.2 | 59.9 ± 3.4 |

TABLE 2

| | Scopolamine-administered group | | |
|---|---|---|---|
| Normal control group | Disease control group | Compound (I) 3.3 mg/kg | Compound (I) 10 mg/kg |
| 73.8 ± 3.0 | 53.3 ± 2.2* | 68.5 ± 2.0# | 68.5 ± 1.6# |

TABLE 3

| | Scopolamine-administered group | |
|---|---|---|
| Normal control group | Disease control group | Donepezil 0.03 mg/kg |
| 71.1 ± 3.3 | 55.0 ± 2.3* | 62.7 ± 3.6 |

TABLE 4

| | Scopolamine-administered group | | |
|---|---|---|---|
| Normal control group | Disease control group | Donepezil 0.1 mg/kg | Donepezil 0.3 mg/kg |
| 71.5 ± 4.8 | 53.9 ± 2.7* | 66.2 ± 4.0 | 70.4 ± 4.8# |

TABLE 5

| | Scopolamine-administered group | | | |
|---|---|---|---|---|
| Normal control group | Disease control group | Donepezil 0.03 mg/kg | Compound (I) 1 mg/kg | Donepezil 0.03 mg/kg and Compound (I) 1 mg/kg |
| 76.4 ± 2.3 | 54.8 ± 3.8* | 57.8 ± 4.0 | 64.9 ± 2.2 | 73.1 ± 2.3 ✕ |

Results

In T2, the rats of the disease control group exhibited a significantly lower percentage of exploration of the novel object than the rats of the normal control group. This means that memory impairment was induced in the rats by scopolamine.

Compound (I) exhibited a significant ameliorative effect on the percentage of exploration of the novel object at 3.3 mg/kg (Table 2), but did not exhibit a significant effect at 1 mg/kg (Table 1). Donepezil hydrochloride exhibited a significant ameliorative effect on the percentage of exploration of the novel object at 0.3 mg/kg (Table 4), but did not exhibit a significant effect at 0.03 mg/kg (Table 3). When the effects of compound (I) and donepezil hydrochloride alone were compared with the effect of their use in combination, in doses that are ineffective with each alone, it was found that the combined treatment group with compound (I) (1 mg/kg) and donepezil hydrochloride (0.03 mg/kg) exhibited a significantly higher percentage of exploration of the novel object than the donepezil hydrochloride (0.03 mg/kg) single drug-treated group (Table 5). This result indicates an augmenting effect on cognitive function by compound (I) when in combination with donepezil hydrochloride.

The invention claimed is:
1. A method for treating Alzheimer's disease, comprising administering (S)-7-(2-methoxy-3,5-dimethylpyridin-4-yl)-1-(tetrahydrofuran-3-yl)-1H-pyrazolo[4,3-c] quinoline-4 (5H)-one represented by formula (I):

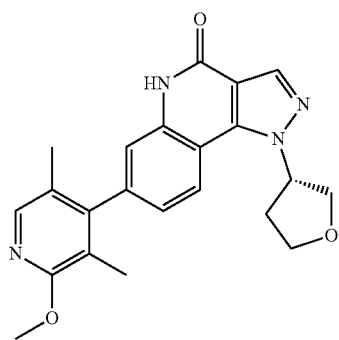

(I)

or a pharmaceutically acceptable salt thereof, and donepezil represented by formula (II):

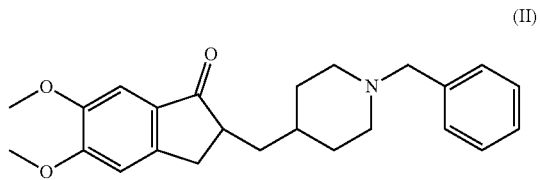 [SMILES: COc1cc2c(cc1OC)C(=O)C(CC1CCN(Cc3ccccc3)CC1)C2]

(II)

or a pharmaceutically acceptable salt thereof to a patient in need thereof.

2. The method according to claim 1, wherein the (S)-7-(2-methoxy-3,5-dimethylpyridin-4-yl)-1-(tetrahydrofuran-3-yl)-1H-pyrazolo[4,3-c]quinoline-4(5H)-one or pharmaceutically acceptable salt thereof, and the donepezil or pharmaceutically acceptable salt thereof are administered simultaneously or separately.

3. The method according to claim 1, wherein the donepezil or pharmaceutically acceptable salt thereof is donepezil hydrochloride.

4. The method according to claim 1, wherein the (S)-7-(2-methoxy-3,5-dimethylpyridin-4-yl)-1-(tetrahydrofuran-3-yl)-1H-pyrazolo[4,3-c] quinoline-4 (5H)-one or pharmaceutically acceptable salt thereof is (S)-7-(2-methoxy-3,5-dimethylpyridin-4-yl)-1-(tetrahydrofuran-3-yl)-1H-pyrazolo[4,3-c] quinoline-4 (5H)-one maleate.

5. The method according to claim 1, wherein the Alzheimer's disease is mild, moderate or severe Alzheimer's disease.

6. A method for treating Lewy body dementia, comprising administering (S)-7-(2-methoxy-3,5-dimethylpyridin-4-yl)-1-(tetrahydrofuran-3-yl)-1H-pyrazolo[4,3-c] quinoline-4 (5H)-one represented by formula (I):

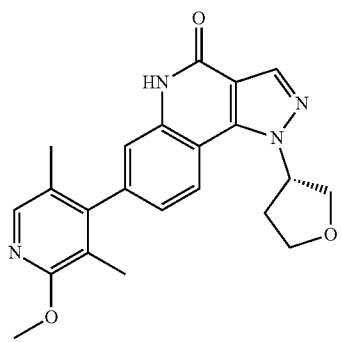

(I)

or a pharmaceutically acceptable salt thereof, and donepezil represented by formula (II):

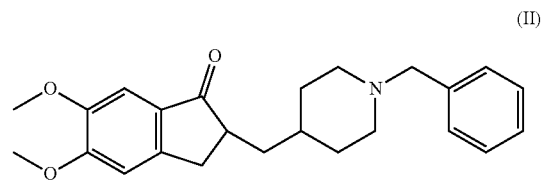 [SMILES: COc1cc2c(cc1OC)C(=O)C(CC1CCN(Cc3ccccc3)CC1)C2]

(II)

or a pharmaceutically acceptable salt thereof to a patient in need thereof.

7. The method according to claim 6, wherein the (S)-7-(2-methoxy-3,5-dimethylpyridin-4-yl)-1-(tetrahydrofuran-3-yl)-1H-pyrazolo[4,3-c]quinoline-4(5H)-one or pharmaceutically acceptable salt thereof, and the donepezil or pharmaceutically acceptable salt thereof are administered simultaneously or separately.

8. The method according to claim 6, wherein the donepezil or pharmaceutically acceptable salt thereof is donepezil hydrochloride.

9. The method according to claim 6, wherein the (S)-7-(2-methoxy-3,5-dimethylpyridin-4-yl)-1-(tetrahydrofuran-3-yl)-1H-pyrazolo[4,3-c] quinoline-4 (5H)-one or pharmaceutically acceptable salt thereof is (S)-7-(2-methoxy-3,5-dimethylpyridin-4-yl)-1-(tetrahydrofuran-3-yl)-1H-pyrazolo[4,3-c] quinoline-4 (5H)-one maleate.

* * * * *